(12) United States Patent
Davis

(10) Patent No.: US 8,592,167 B2
(45) Date of Patent: Nov. 26, 2013

(54) ENZYME DETECTION DEVICE

(75) Inventor: Paul James Davis, Felmersham (GB)

(73) Assignee: Mologic Ltd (GB)

( * ) Notice: Subject to any disclaimer, the term of this patent is extended or adjusted under 35 U.S.C. 154(b) by 257 days.

(21) Appl. No.: 12/674,603

(22) PCT Filed: Aug. 26, 2008

(86) PCT No.: PCT/GB2008/002889
§ 371 (c)(1),
(2), (4) Date: Mar. 6, 2012

(87) PCT Pub. No.: WO2009/024805
PCT Pub. Date: Feb. 26, 2009

(65) Prior Publication Data
US 2012/0149032 A1    Jun. 14, 2012

(30) Foreign Application Priority Data
Aug. 23, 2007   (GB) .................................. 0716492.4

(51) Int. Cl.
G01N 33/53 (2006.01)
G01N 33/536 (2006.01)
G01N 33/543 (2006.01)

(52) U.S. Cl.
USPC ............................ 435/7.1; 435/7.9; 435/7.92

(58) Field of Classification Search
None
See application file for complete search history.

(56) References Cited

U.S. PATENT DOCUMENTS

| 5,759,787 A | 6/1998 | Strulovici | |
|---|---|---|---|
| 2003/0113713 A1* | 6/2003 | Glezer et al. | 435/5 |
| 2006/0003394 A1 | 1/2006 | Song | |

FOREIGN PATENT DOCUMENTS

| EP | 0392808 A2 | 10/1990 | | |
|---|---|---|---|---|
| EP | 1 557 474 A1 | 7/2005 | | |
| EP | 1736776 A2 | 12/2006 | | |
| EP | 1889919 A1 | 2/2008 | | |
| GB | 2435511 A | 8/2007 | | |
| GB | 2437311 A | 10/2007 | | |
| WO | WO-0050630 A2 | 8/2000 | | |
| WO | WO-0050896 A1 | 8/2000 | | |
| WO | WO-0075167 A2 | 12/2000 | | |
| WO | WO-0127624 A2 | 4/2001 | | |
| WO | WO-03076894 A2 | 9/2003 | | |
| WO | WO-2006123789 A1 | 11/2006 | | |
| WO | WO2007/096637 | * | 2/2007 | .......... G01N 33/558 |
| WO | WO/2007/060599 | * | 5/2007 | .......... G01N 33/543 |

OTHER PUBLICATIONS

LaBorde et al., (IVD Technology, 2002).*
Dupont et al., Analytical Biochemistry, 2003; 317, pp. 240-246) retrieved from URL: www.ivdtechnology.com/print/231.*
International Search Report for GB0716492.4 dated of search Apr. 25, 2008.
United Kingdom Search Report for GB0716492.4 dated of search Apr. 25, 2008.
Zhang, Jianhua, et al.; "Mast cell tryptase does not alter matrix metalloproteinase expression in human dermal fibroblasts: Further evidence that proteolytically-active tryptase is a potent fibrogenic factor," Journal of Cellular Physiology, vol. 181, No. 2: 312-318 (Nov. 1999).
International Search Report for PCT/GB2008/002889 dated Jan. 13, 2009.

* cited by examiner

*Primary Examiner* — Jacob Cheu
*Assistant Examiner* — Carmencita M Belei
(74) *Attorney, Agent, or Firm* — Foley Hoag LLP

(57) ABSTRACT

An enzyme detection device (1) for detecting the presence, in a sample, of an enzyme capable of modifying a provided substrate (10). The device (1) comprises a substrate which has a modification region (14) that is sensitive to modification by the enzyme from an unmodified state to a modified state. The device (1) further comprises a substrate recognition molecule (16) which binds the modification region (14) in either the modified or the unmodified state. The modification region 14 of the substrate is preferentially bound by the substrate recognition molecule (16) as compared with the enzyme when mixed. The device further comprises a detectable label (18) coupled to the substrate recognition molecule (17).

9 Claims, 3 Drawing Sheets

ENZYME DETECTION DEVICE

This application is a 371 national stage application of PCT/GB2008/002889, filed Aug. 26, 2008, which claims priority to GB 0716492.4, filed Aug. 23, 2007. The entire contents of each of these applications are hereby incorporated by reference.

SEQUENCE LISTING

The instant application contains a Sequence Listing which has been submitted in ASCII format via EFS-Web and is hereby incorporated by reference in its entirety. Said ASCII copy, created on May 30, 2013, is named P180714US00_ST25.txt and is 1 KB in size.

BACKGROUND OF THE INVENTION

The present invention relates to an enzyme detection device and, more specifically, an enzyme detection device for detecting an enzyme capable of modifying a provided substrate that is recognisable by a specific binding molecule in either its modified or unmodified state. The invention also relates to a method of detecting an enzyme capable of modifying a substrate.

There are many clinical and research situations where it is useful to be able to detect the presence, in a sample, of an enzyme that has a particular catalytic activity. One example of such an enzyme is a protease, which digests proteins by hydrolysing and cleaving peptide bonds. Thus a protein which is degraded by a protease is cleaved into two or more smaller peptides. Another example is a sialidase which will cleave a sialic acid moiety from a larger carbohydrate.

A diagnostic test kit is disclosed in US2006/0003394 which detects an enzyme in a sample. The kit comprises "reactive complexes" which each comprise a target ligand joined to a reporter and a specific binding member. The target ligand is cleavable by the enzyme to be detected in order to release the reporter. The mixture of the reactive complexes and the sample is subsequently applied to a chromatographic medium. The chromatographic medium comprises a first detection zone which is capable of capturing the specific binding member on the target ligand and a second detection zone which his capable of binding the reporter. Therefore, in use, the mixture of the sample and reactive complexes is applied to the chromatographic medium and flows firstly through the first detection zone and then through the second detection zone. At the first detection zone the target ligand is captured. Any enzyme in the sample cleaves the reporter from the target ligand and the cleaved reporter is captured at the second detection zone, leaving any un-cleaved reporter remaining attached to the target ligand, at the first detection zone. Therefore, the presence of the enzyme in the sample is determined by the presence of the reporter at the second detection zone (or the absence of the reporter from the first detection zone). One problem with the kit disclosed in US2006/0003394 is that the kit can tend to give inaccurate results because the enzyme continues to be active while the mixture is flowing along the chromatographic medium. The enzyme continues to cleave the reporter from the target ligand while the reactive complexes are immobilised at the first capture zone. Thus, the signal at the first detection zone and the second detection zone can tend to vary over time, there being no clear end point to the reaction.

Another problem with the kit of US2006/0003394 is that it can only detect an enzyme that cleaves the target ligand and is not able to detect enzymes that have other effects such as adding moieties to a target ligand (e.g. phosphorylation or glycosylation).

A further problem with the kit of US2006/0003394 is that it cannot detect the activity of enzymes that have to cleave the terminus of the target ligand, such as an exopeptidase, or an exocarbohydrase, because the requirement to join a reporter to the terminus would change the chemical nature of the terminus to an extent that would prevent interaction with the enzyme's active site.

SUMMARY OF THE INVENTION

The present invention seeks to alleviate one or more of the above problems.

According to one aspect of the present invention, there is provided an enzyme detection device for detecting the presence in a sample of an enzyme capable of modifying a provided substrate comprising:
(i) a substrate comprising a modification region sensitive to modification by the enzyme from an unmodified state to a modified state;
(ii) a substrate recognition molecule capable of specifically binding the modification region in either the modified or the unmodified state, the binding site of the substrate recognition molecule being such that the substrate recognition molecule and the enzyme competitively bind the modification region when mixed; and
(iii) a detectable label couplable to the substrate recognition molecule.

According to another aspect of the present invention, there is provided an enzyme detection device for detecting the presence in a sample of an enzyme capable of modifying a provided substrate comprising:
(i) a substrate comprising a modification region sensitive to modification by the enzyme from an unmodified state to a modified state;
(ii) a substrate recognition molecule capable of specifically binding the modification region of the substrate in the unmodified state, the binding site of the substrate recognition molecule being such that the modification region of the substrate is preferentially (or competitively) bound by said substrate recognition molecule as compared with the enzyme when mixed; and
(iii) a detectable label couplable to the substrate recognition molecule.

Advantageously, the affinity of the substrate recognition molecule for the substrate comprises a relatively low dissociation rate ($k_d$).

Preferably, the affinity of the substrate recognition molecule for the substrate comprises a relatively low dissociation rate ($k_d$) and a relatively high association rate ($k_a$).

Preferably, the dissociation rate ($k_d$) of the substrate recognition molecule is between $10^4.s^{-1}$ and $10^{-7}.s^{-1}$, more preferably between $10^{-5}.s^{-1}$ and $10^{-6}.s^{-1}$.

Preferably, the association rate ($k_3$) of the substrate recognition molecules is between $10^5.s^{-1}$ and $10^9.s^{-1}$, more preferably between $10^7.s^{-1}$ and $10^8.s^{-1}$.

Advantageously, the substrate recognition molecule has a lower dissociation rate ($k_d$) and a higher association rate ($k_a$) for the substrate than the enzyme has for the substrate.

Conveniently, the substrate further comprises an attachment region and the enzyme detection device further comprises a solid support, the attachment region being attachable to the solid support.

Preferably, the enzyme detection device further comprises a chromatographic medium.

Advantageously, the substrate further comprises an attachment region attachable to the chromatographic medium.

Conveniently, the chromatographic medium comprises a first capture recognition molecule, immobilised on or in the chromatographic medium and capable of binding the attachment region of the substrate.

Preferably, the chromatographic medium further comprises a second capture recognition molecule, immobilised on or in the chromatographic medium, and capable of binding the substrate recognition molecule, optionally in combination with a fragment of the substrate.

Advantageously, the first capture recognition molecule and the attachment region and/or the second capture recognition molecule and the substrate recognition molecule are each two halves of a binding pair wherein the binding pair is: an antigen and antibody or antigen-binding fragment specific therefor; biotin and avidin, streptavidin, neutravidin, or captavidin; protein A and G; a carbohydrate and a lectin; two complementary nucleotide sequences; an effector and a receptor molecule; a hormone and a hormone binding protein; an enzyme cofactor and an enzyme; an enzyme inhibitor and an enzyme; a cellulose binding domain and cellulose fibres; immobilised aminophenyl boronic acid and cis-diol bearing molecules; xyloglucan and cellulose fibres and analogues, derivatives and fragments thereof.

Conveniently, the substrate recognition molecule is an antibody or antigen binding fragment thereof; a lectin; a nucleotide sequence; a receptor molecule; or a hormone binding protein capable of binding the modification region in either the modified or the unmodified state.

Alternatively, the substrate recognition molecule is avidin, streptavidin, neutravidin, or captavidin capable of binding unmodified biotin.

Preferably, the enzyme is a hydrolase, preferably a peptidase, lipase, nuclease, carbohydrase, phosphatase, sulphatase, neuraminidase, esterase, DNAase or RNAase.

Alternatively, the enzyme is a kinase, a glycosyl transferase, an oxidase, a reductase or a transaminase.

Advantageously, the enzyme detection device further comprises a detectable label attached to the substrate recognition molecule.

Conveniently, the detectable label is covalently bound to the substrate recognition molecule.

Preferably, the label is a fluorophore, a gold particle, a chromogen, a luminescent compound; a radioactive compound; a visible compound, a liposome or other vesicle containing signal producing substances, an electroactive species or a combination of an enzyme and its substrate.

Advantageously, the enzyme detection device comprises first and second substrates, each comprising a modification region, the modification region of the first substrate being sensitive to modification by a first enzyme, the modification region of the second substrate being sensitive to modification by a second enzyme.

According to another aspect of the present invention, there is provided a method of detecting an enzyme capable of modifying a substrate comprising the steps of:
(i) providing a substrate comprising a modification region sensitive to modification by the enzyme from an unmodified state to a modified state;
(ii) providing a sample suspected of containing the enzyme;
(iii) providing a substrate recognition molecule that specifically binds the modification region in either the unmodified state or the modified state, the binding site of the substrate recognition molecule being such that the substrate recognition molecule and the enzyme competitively bind the modification region when mixed;
(iv) mixing the sample and substrate such that at least some of the enzyme in the sample modifies the substrate; and
(v) bringing the substrate and the substrate recognition molecule into contact and detecting the interaction between the substrate and the substrate recognition molecule.

According to a further aspect of the present invention, there is provided a method of detecting an enzyme capable of modifying a substrate comprising the steps of:
(i) providing a substrate comprising a modification region sensitive to modification by the enzyme from an unmodified state to a modified state;
(ii) providing a sample suspected of containing the enzyme;
(iii) providing a substrate recognition molecule that specifically binds the modification region in the unmodified state, the binding site of the substrate recognition molecule being such that the modification region of the substrate is preferentially (or competitively) bound by said substrate recognition molecule as compared with the enzyme when mixed;
(iv) mixing the sample and substrate such that at least some of the enzyme in the sample modifies the substrate; and
(v) bringing the substrate and the substrate recognition molecule into contact and detecting the interaction between the substrate and the substrate recognition molecule.

Advantageously, the affinity of the substrate recognition molecule for the substrate comprises a relatively low dissociation rate ($k_d$).

Preferably, the affinity of the substrate recognition molecule for the substrate comprises a relatively low dissociation rate ($k_d$) and a relatively high association rate ($k_a$).

Preferably, the dissociation rate ($k_d$) of the substrate recognition molecule is between $10^{-4}.s^{-1}$ and $10^{-7}.s^{-1}$, more preferably between $10^{-5}.s^{-1}$ and $10^{-6}.s^{-1}$.

Preferably, the association rate ($k_a$) of the substrate recognition molecules is between $10^5.s^{-1}$ and $10^9.s^{-1}$, and more preferably between $10^7.s^{-1}$ and $10^8.s^{-1}$.

Advantageously, the substrate recognition molecule has a lower dissociation rate ($k_d$) and a higher association rate ($k_a$) for the substrate than the enzyme has for the substrate.

Conveniently, the substrate further comprises an attachment region and wherein step (i) further comprises the step of providing a solid support and attaching the attachment region of the substrate to the solid support.

Preferably, step (i) comprises providing a first capture recognition molecule, capable of binding the attachment region, on the solid support.

Advantageously, (v) further comprises depositing the substrate and the substrate recognition molecule on or in a chromatographic medium.

Conveniently, the chromatographic medium comprises a first capture recognition molecule immobilised on or in the chromatographic medium, the substrate further comprising an attachment region, the first capture recognition molecule being capable of binding the attachment region and the method further comprising the step of detecting the immobilisation of the substrate recognition molecule at the first capture recognition molecule.

Preferably, the chromatographic medium further comprises a second capture recognition molecule immobilised on or in the chromatographic medium, the second capture recognition molecule being capable of binding the substrate recognition molecule, optionally in combination with a fragment of the substrate, wherein the method further comprises the step of detecting the presence of the substrate recognition molecule at the second capture recognition molecule.

Advantageously, the first capture recognition molecule and the attachment region and/or the second capture recognition molecule and the substrate recognition molecule are two halves of a binding pair, wherein the binding pair is an antigen, and an antibody or antigen binding fragment thereof; biotin and avidin, streptavidin, neutravidin, or captavidin; an immunoglobulin (or appropriate domain thereof) and protein A and G; a carbohydrate and a lectin; two complementary nucleotide sequences; an effector and a receptor molecule; a hormone and a hormone binding protein; an enzyme cofactor and an enzyme; an enzyme inhibitor and an enzyme; a cellulose binding domain and cellulose fibres; immobilised aminophenyl boronic acid and cis-diol bearing molecules; or xyloglucan and cellulose fibres and analogues, derivatives and fragments thereof.

Conveniently, the substrate recognition molecule is an antibody or antigen binding fragment thereof a lectin; a nucleotide sequence; a receptor molecule; or a hormone binding protein capable of binding the modification region in either the modified or the unmodified state.

Alternatively, the substrate recognition molecule is avidin, streptavidin, neutravidin, or captavidin capable of binding unmodified biotin.

Preferably, the enzyme is a hydrolase, preferably a peptidase, lipase, nuclease, homo- or hetero-oligosaccharidedase, homo or hetero-polysaccharidase, carbohydrase, phosphatase, sulphatase, neuraminidase, esterase, DNAase or RNAase.

Alternatively, the enzyme is a kinase, a glycosyl transferase, an oxidase, a reductase or a transaminase.

Advantageously, the method further comprises the step of providing a label attached to the substrate recognition molecule and wherein step (v) comprises detecting the presence of the label.

Conveniently, the label is covalently bound to the substrate recognition molecule.

Preferably, the label is a fluorophore, a gold particle, a chromogen, a luminescent compound; a radioactive compound; a visible compound, a liposome or other vesicle containing signal producing substances; an electroactive species; or a combination of an enzyme and its substrate.

Advantageously, step (i) comprises providing first and second substrates, each comprising a modification region, the modification region of the first substrate being sensitive to a first enzyme, the modification region of the second substrate being sensitive to modification by a second enzyme and wherein step (v) comprises detecting the interaction between first and second substrates and the substrate recognition molecule.

Conveniently, step (iii) comprises providing first and second substrate recognition molecules, each specifically binding the modification region of the first and second substrates, respectively, in either the modified or the unmodified state, the binding site of the first and second substrate recognition molecules being such that the modification region of the first substrate is preferentially (or competitively) bound by said first substrate recognition molecule as compared with the first enzyme, and the modification region of the second substrate is preferentially (or competitively) bound by said second substrate recognition molecule as compared with the second enzyme, and wherein step (v) comprises detecting the interaction between the first and second substrates and the first and second substrate recognition molecules.

Thus aspects of the invention provide an enzyme detection device for detecting the presence, in a sample, of an enzyme capable of modifying a provided substrate which has a modification region that is sensitive to modification by the enzyme from an unmodified state to a modified state. The device transforms the enzyme activity into an affinity binding assay wherein the presence of enzyme activity is expressed as bound label, such as the relative intensity of a signal line. In this method, unmodified substrate is detected and bound by a substrate recognition molecule which binds a modification region of the substrate in the unmodified state. In use, the substrate is preferentially (or competitively) bound by the substrate recognition molecule in comparison with the enzyme molecule when mixed. This is because the substrate recognition molecule has a lower dissociation rate ($k_d$) than the enzyme. Typically enzymes have a high dissociation rate ($k_d$) so that the product leaves the enzyme active site quickly in order to obtain a high turnover. The substrate recognition molecule also has a high association rate ($k_a$) for the substrate to further enable it to bind to the substrate preferentially to the enzyme binding the substrate. Such dissociation and association rates are measured using technology such as Biacore. The affinity of the substrate recognition molecule for the enzyme is measurably higher than the affinity of the enzyme for the substrate, i.e. in the presence of both the substrate recognition molecule and the enzyme there is no noticeable decrease in the amount of substrate present in the mixture. The device further comprises a detectable label coupled to the substrate recognition molecule.

The substrate recognition molecule of the present invention sequesters the modifiable region of the substrate, and in doing so it prevents the enzyme from modifying the substrate further. This feature is advantageous for use in end-point assays (cf. kinetic assays). It enables the assay procedure to be tightly controlled because the catalytic activity of the enzyme can be stopped precisely after a predetermined period of time. This prevents variable and uncontrolled run-on of the substrate transformation activity, i.e., sequestering of the substrate modification region by the substrate recognition molecule accurately controls and defines the end point of the assay.

BRIEF DESCRIPTION OF THE INVENTION

In order that the present invention may be more fully understood and so that further features thereof may be appreciated, embodiments of the invention will now be described, by way of example, with reference to the accompanying figures in which.

DETAILED DESCRIPTION OF THE INVENTION

Figure 1:
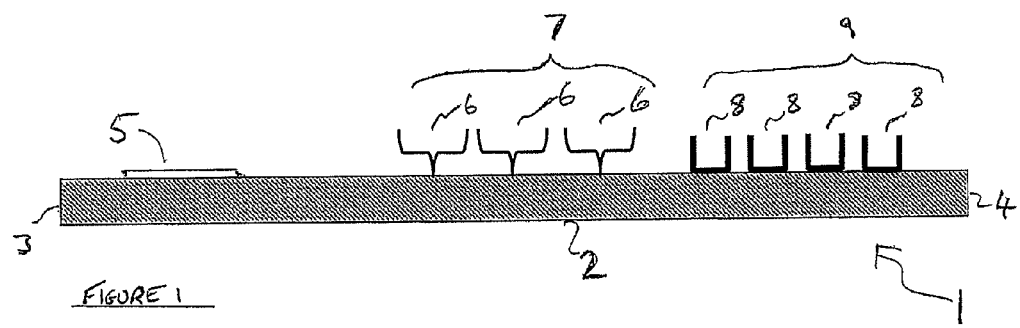
FIG. 1 is a schematic view of one component of an enzyme detection device in accordance with one embodiment of the present invention.

Referring to FIG. 1, a schematic cross-sectional view of some components of an enzyme detection device 1 for detecting an analyte enzyme are shown. The enzyme detection device 1 comprises a nitrocellulose test strip 2 which forms a chromatographic medium. The test strip 2 has upstream and downstream ends 3, 4. Adjacent the upstream end 3 of the test strip 2 there is provided a sample receiving zone 5 comprising an absorbent pad. Further towards the downstream end 4 of the test strip 2 there are provided a plurality of first capture recognition molecules 6 immobilised on the surface of the test strip 2. The first capture recognition molecules to form a first detection zone 7. Further towards the downstream end 4 of the test strip 2, from the first detection zone 7, there is provided a plurality of second capture recognition molecules 8 immobilised on the surface of the test strip 2. The second capture recognition molecules 8 form a second detection zone 9.

Figure 2:
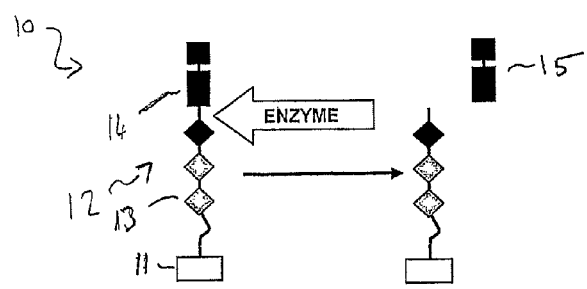
FIG. 2 is a diagram of the action of another component of an enzyme detection device in accordance with an embodiment of the present invention.
Figure 3:
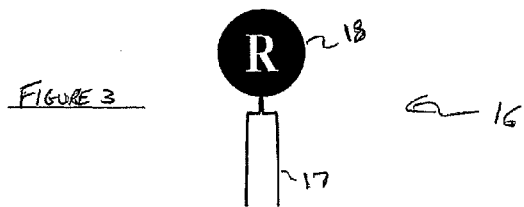
FIG. 3 is a schematic view of another component of an enzyme detection device in accordance with one embodiment of the present invention.

Referring now to FIG. 2, another component of the enzyme detection device will be described, namely a substrate 10. The substrate 10 comprises an unmodifiable ligand 11 connected to a second region 12. The unmodifiable ligand 11 is capable of being recognised and captured by the first capture recognition molecules 6 of the first detection zone 7. That is to say, the unmodifiable ligand 11 forms one half of a binding pair, the other half of the binding pair being one of the first capture recognition molecules 6. The second region 12 comprises a second ligand (known as the "modification region") 14 which is connected to the unmodifiable ligand 11 via an optional, inert core (spacer) structure 13. The second ligand 14 is modifiable by the analyte enzyme. As shown in FIG. 2 the analyte enzyme is a protease that modifies the second ligand 14 by cleaving a part of the structure, to release a fragment 15. However, in other embodiments, a different modification of the modification region 14 (i.e. the second ligand) is made by the enzyme, for example, the addition of a phosphate group. Other exemplary modifications include glycosyl transferases that transfer a sugar group from a donor molecule to a receiver site, oxidases that oxidise a target site, reductases that reduce a target site and transaminases that transfer amino groups between amino acids and keto-acids. Referring to FIG. 3, a further component of the enzyme detection will now be described. A binding member 16 comprises a substrate recognition molecule 17 which is capable of specifically binding the modification region 14 of the substrate 10. Furthermore, the substrate recognition molecule 17 binds the substrate 10 at the region (the modification region 14) that is bound and modified by the enzyme to be detected. That is to say, the modification region 14 of the substrate is preferentially (or competitively) bound by the substrate recognition molecule 17 as compared with the enzyme if the enzyme and the substrate recognition molecule are mixed with the modification region 14. Additionally, the substrate recognition molecule 17 may have a higher binding affinity for the modification region 14 than does the enzyme. Consequently, once the modification region 14 has been bound by the substrate recognition molecule 17, the enzyme is unable to bind the modification region 14 and therefore cannot catalyse the modification of the modification region 14.

Coupled to the substrate recognition molecule 17 is a detectable label or reporter 18, which is, for example, a fluorophore.

Figure 4:
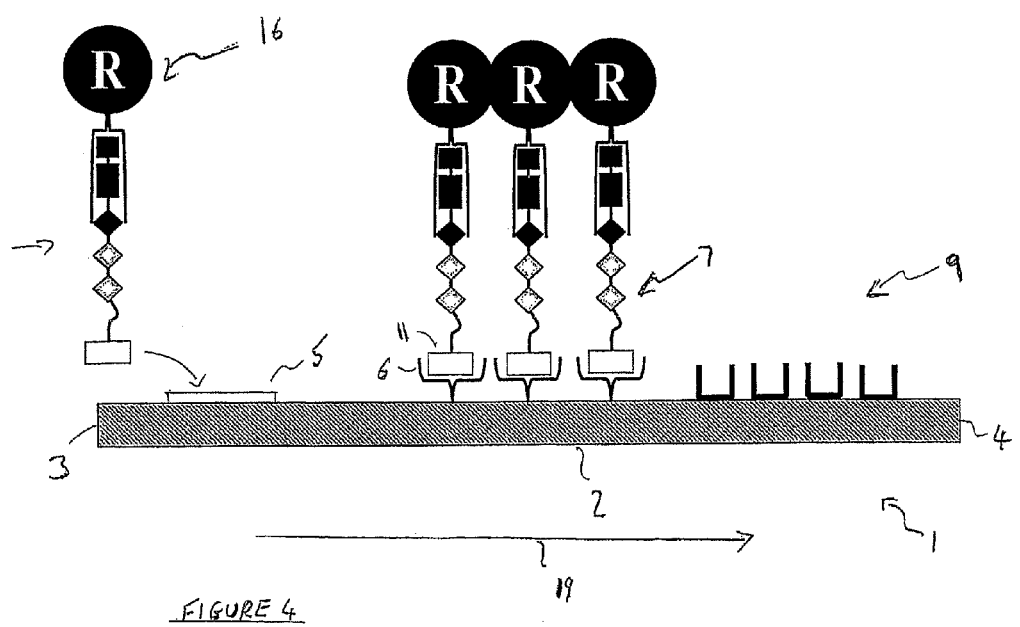
FIG. 4 is a schematic view of an enzyme detection device in accordance with one embodiment of the present invention, in use.

The use of the enzyme detection device 1 in accordance with this embodiment will now be described with reference to FIG. 4. In this example, a sample is provided which does not contain the enzyme. The sample is mixed with the substrate 10 under conditions which would permit any enzyme in the sample to modify the modification region 14. As previously stated, in this particular example, the sample does not contain the enzyme and therefore no modification of the modification region 14 takes place. The mixture of the sample and the substrate 10 is then contacted with the binding member 16 under conditions which allow the binding member 16 to bind the substrate 10. The mixture of the sample, substrate 10, and binding member 16 is then deposited on the sample receiving zone 5 on the test strip 2. Due to the chromatographic nature of the test strip 2, the mixture flows along and/or through the test strip 2 along a liquid flow path from the upstream end 3 of the test strip 2 to the downstream end 4 of the test strip 2; that is to say in the direction of the arrow 19.

The mixture comes into contact with the first detection zone 7 and the unmodifiable ligand 11 of each substrate 10 binds to a capture recognition molecule 6 of the first detection zone 7. Thus the substrate 10 becomes immobilised at the first detection zone 7. Furthermore, since the binding member 16 is bound to the substrate 10, the binding member 16 also becomes immobilised at the first detection zone 7. Although other components of the mixture continue to flow in the direction of the arrow 19 along the test strip 2, there is little or none of the binding member 16 to bind at the second detection zone 9. Therefore, the absence of the enzyme from the sample is indicated by the presence of the reporter 18 at the first detection zone 7 and the absence of the reporter 18 from the second detection zone 9.

Figure 5:
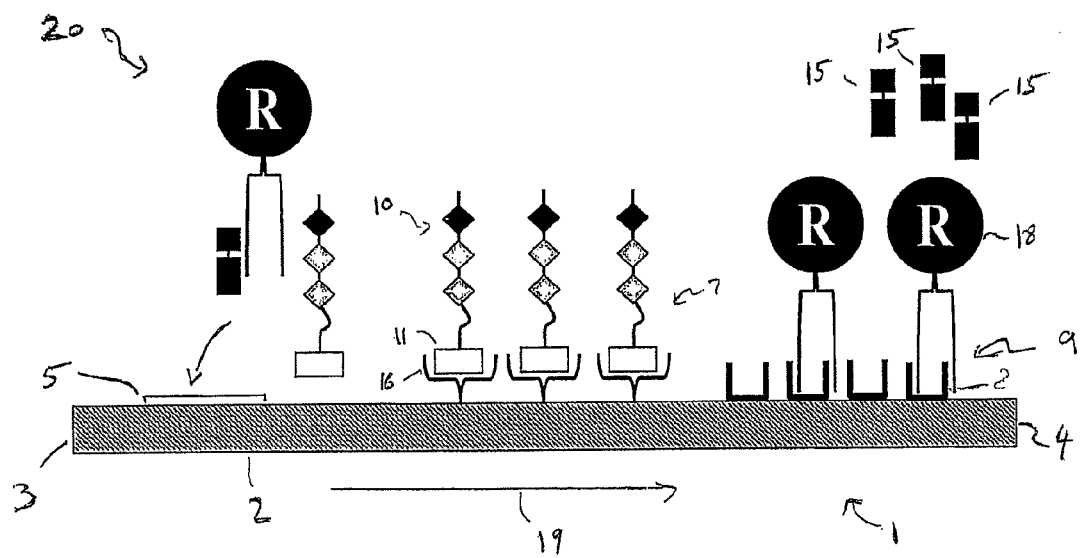
FIG. 5 is a schematic view of an enzyme detection device in accordance with one embodiment of the present invention, in use.

Referring now to FIG. 5, an enzyme detection device 1 in accordance with this embodiment of the present invention will be described in use, detecting the presence of the enzyme in a sample. The substrate 10 is mixed with the sample under conditions such that the enzyme is able to modify the modification region 14 of the substrate 10. In this embodiment, the enzyme cleaves the modification region 14 to release the fragment 15. After a predetermined period of time, the mixture of the substrate 10 and the enzyme is contacted with the binding member 16 under conditions such that the binding member 16 binds any of the unmodified modification region 14. In doing so, the binding member 16 blocks the enzyme from the modification region 14, bringing an end to the catalytic activity of the enzyme. More specifically, in this embodiment the substrate 10 ceases to be cleaved by the enzyme.

The mixture 20 is then deposited on the sample receiving zone 5 and flows along or through the test strip 2 in the direction of the arrow 19. The sample 20 firstly comes into contact with the first detection zone 7 whereat the unmodifiable ligand 11 of each substrate 10 binds the first capture recognition molecule. Thus the modified and unmodified substrate 10 is immobilised at the first detection zone 7. Furthermore, the binding members 16 are not able to bind the substrate 10, because the modification region 14 has been cleaved with the loss of fragment 15. The binding members 16 are specific for the unmodified (that is to say "intact" in this embodiment) modification region and cannot bind to incomplete ligand 14. Therefore, the remainder of the sample 20 continues to flow along the test strip 2 in the direction of the arrow 19 until it comes into contact with the second detection zone 9 whereat the substrate recognition molecules 16 are bound and immobilised by the second capture recognition molecules 8. Thus the binding members 16, including the reporters 18, are immobilised at the second detection zone 9. Therefore, the presence of the enzyme in the sample is indicated by the presence of the reporter 18 immobilised at the second detection zone 9 and the absence of the reporter 18 from the first detection zone 7.

It is to be appreciated that it is not essential to the invention that the modification to the modification region 14 is a cleavage thereof. For example in some other embodiments, the enzyme to be detected modifies the modification region 14 by adding a moiety to the modification region 14. The presence of the enzyme in the sample still results in the binding member 16 being immobilised at the second detection zone 9 rather than the first detection zone 7 but with the difference that no fragments 15 are released. Instead, the substrate 10 remains intact but the binding member 16 is unable to bind the modification region in its modified state and therefore flows through the first detection zone 7 on to the second detection zone 9 where it is bound.

Furthermore, it is also disclosed herein a device and a method wherein the binding member 16 is specific for the modification region in its modified state. For example, in an embodiment in which the enzyme modifies a modification region 14 by adding a moiety to it, the binding member 16 binds the modification region 14 when the moiety is present but not when it is absent. Thus the binding member 16 is immobilised at the second detection zone 9 if the enzyme is absent from the sample and at the first detection zone 7 if the enzyme is present in the sample. Therefore, the presence of the enzyme in a sample is indicated by the presence of the reporter 18 immobilised at the first detection zone 7 and the absence of the reporter 18 from the second detection zone 9.

In some embodiments, the relative concentration of the reporter 18 at the first and second detection zones 7, 9 is assessed to indicate the relative concentration of the enzyme in the sample. For example, in embodiments where the reporter 18 is a visible label such as a gold article the relative intensity of the label is compared between the first and second detection zones 7, 9.

In embodiments of the present invention, the enzyme to be detected may be a hydrolase. For example the enzyme may be a protease, a peptidase, lipase, nuclease, homo- or hetero-oligosaccharidedase, homo or hetero-polysaccharidase, carbohydrase, phosphatase, sulphatase, neuraminidase (e.g. a sialidase), esterase, DNAase or RNAase. In other embodiments, the enzyme modifies the modification region in a manner other than by cleavage thereof. For example, the enzyme may be a kinase, glycosyl transferase, reductase or transaminase.

The modification region 14, must, of course, be appropriate for the enzyme to be detected. That is to say if the enzyme is a protease then the modification region 14 must be a peptide which the enzyme cleaves. As another example, if the enzyme is sialidase, then the modification region 14 may comprise a sialyl lewis antigen. Other modification regions include nucleic acids, carbohydrates, lipids, esters and glycoproteins. In the case of the enzyme being a glycosyl transferase, a sugar group is transferred from a donor molecule to a receiver site. Where the enzyme is an oxidase, a target site is oxidised (e.g. glucose is oxidised to gluconic acid). If the enzyme is a reductase, it reduces a target site (e.g. quinine reductase reduces quinones to phenols). Transaminases transfer amino groups between amino acids and keto-acids.

The capture recognition molecules 6 and the unmodifiable ligands 11 may be any suitable components of a specific binding pair. For example they may be: an antigen, and an antibody or antigen binding fragment thereof; biotin and avidin, streptavidin, neutravidin, or captavidin; an immunoglobulin (or appropriate binding domain thereof) and protein A and G; a carbohydrate and a lectin; two complementary nucleotide sequences; an effector and a receptor molecule; a hormone and a hormone binding protein; an enzyme cofactor and an enzyme; an enzyme inhibitor and an enzyme; a cellulose binding domain and cellulose fibres; immobilised aminophenyl boronic acid and cis-diol bearing molecules; xyloglucan and cellulose fibres, and analogues, derivatives and fragments thereof.

It is particularly preferred that the unmodifiable ligand 11 is a biotin moiety and the first capture recognition molecule is a streptavidin moiety, immobilised on the surface of the test strip 2.

The substrate recognition molecule 17 is preferably an antibody or an antigen binding fragment thereof which is specific for the modification region 14. Such antibodies are created so that their binding assay performance, i.e. the $k_d$ and $k_a$ is optimal for the desired assay, e.g. a high association rate and a low dissociation rate. This is done by means of immunisation techniques familiar to those skilled in the art. High affinity antibodies are produced by repeatedly administering decreasing concentrations of antigen to the animal. Typically, goats and sheep are used to produce high affinity antibodies.

In other embodiments, the substrate recognition molecule 17 is a lectin; a nucleotide sequence; a receptor molecule; or a hormone binding protein capable of binding the modification region in either the modified or the unmodified state. Alternatively, any of the specific binding molecule pairs described above may be used, provided that the substrate recognition molecule 17 recognises a suitable target ligand that can be incorporated into substrate 10 and still be modified by the analyte enzyme in such a way as to change the ability of substrate recognition molecule 17 to interact with the modification region 14. For example, in embodiments where the modification region comprises biotin, the substrate recognition molecule may be avidin, streptavidin, neutravidin, or captavidin capable of binding unmodified biotin but not capable of binding biotin that has been modified by the action of the enzyme to be detected. It is particularly preferred that the substrate recognition molecules 17 are sheep antibodies and the second capture recognition molecules 8 are anti-sheep antibodies.

In some embodiments of the present invention, the binding member 16 is dried into the structure of the test strip 2, either in the sample receiving zone 5 or between the sample receiving zone 5 and the first detection zone 7. In these embodiments, the sample is mixed with a substrate 10 under conditions which allow the enzyme to modify the modification region 14 of the substrate 10. The mixture is then applied to the sample receiving zone 5 and comes into contact with the binding member 16 on the surface of the test strip 2. That is to say, there is no mixing of the sample with the binding member 16 prior to depositing of the sample on the test strip 2.

In some embodiments, a soluble barrier is provided on the test strip 2, just downstream of the sample receiving zone 5. The soluble barrier is impermeable to the mixture of the sample and substrate for a predetermined period of time, after which the barrier is breached and the mixture continues to flow along the test strip. It is particularly preferred to combine this feature with the feature of the binding member 16 being dried onto the test strip 2 just downstream of the soluble barrier. In such an embodiment, the sample and substrate are provided with sufficient time to mix and for any enzyme to modify the modification region 14 before the mixture dissolves the soluble barrier and comes into contact with the binding member 16 which binds the modification region 14 and prevents the enzyme from catalysing any further reaction at the modification region 14. The test strip 2 then operates as described above. The soluble barrier may be, for example, made from PVA, particularly low Molecular Weight (MW) PVA, or cold-water soluble gelatine.

The reporter 18 in any embodiment may be any substance which is capable of directly or indirectly generating a detectable signal. A suitable reporter is a chromogen, luminescent compound (e.g. fluorescent or phosphorescent); radioactive compound; visible compound (e.g. latex or a metallic particle such as gold), liposome or other vesicle containing signal producing substances; an electroactive species; or a combination of an enzyme and its substrate. A preferred reporter is gold particles which accumulate to form a zone visible to the naked eye at the first and/or second detection zone 7, 9 (see FIG. 1). It is also to be appreciated that in some embodiments of the present invention, the substrate recognition molecule 17 is not permanently coupled to the reporter 18 but is instead couplable to it via a specific binding pair as described above.

In certain embodiments, the enzyme detection device 1 comprises two different substrates 10, each having a modification region 14 sensitive to modification by a different enzyme. In some embodiments, both substrates 10 are otherwise identical so that the test strip 2 provides the same signal irrespective of which enzyme is present in the sample. In other embodiments, first and second binding members 16 are provided, each specific for the modification region 14 of one of the substrates 10 but not the other. The modification region 14 of one substrate is preferentially (or competitively) bound by the first binding member 16 as compared with one enzyme, while the modification region 14 of the other substrate is preferentially (or competitively) bound by the second binding member 16 as compared with the other enzyme. Furthermore, the reporter 18 of the first binding member 16 provides a different signal from the reporter 18 of the second binding member 16. Thus the presence of each enzyme can be distinguished by the presence of either signal. In a further embodiment, first and second binding members are provided, as in the previous embodiment except that both binding members carry the same reporter 18 and the second detection zone is supplemented with a third detection zone. The second and third detection zones have second and third capture recognition molecules, respectively. The second and third capture recognition molecules are specific for the first and second binding members respectively. Thus the presence of the either enzyme is distinguishable by the presence or absence of the reporter 18 at either the second or third capture zone.

In some variants of the embodiments where first and second binding members 16 are provided, the enzyme detection device 1 comprises a single sample receiving zone 5 which is in fluid communication with first and second test strips (arranged, for example, parallel to each other or radiating outwardly from the sample receiving zone 5). The first test strip has a first detection zone 7 that binds the first substrate and a second detection zone 9 which binds the binding member 16 that is specific for the first substrate. Similarly, the second test strip has a first detection zone 7 that binds the second substrate and a second detection zone 9 which binds the binding member 16 that is specific for the second substrate. In this way, the first and second test strips separately provide results indicating the presence or absence of the first and second enzymes in a sample.

In the specific embodiments described above, the device comprises a chromatographic medium in the manner of the test strip 2. However, in alternative embodiments, a chromatographic medium is not provided. For example, in one embodiment, the first capture recognition molecules 6 are immobilised on a solid support such as a column or beads. The sample is mixed with the substrate 10 and subsequently with the binding members 16 as in the previously described embodiments. The mixture of the sample, substrate 10 and binding member 16 is then washed over the support, allowing the specific binding members 11 to bind the capture recognition molecules 6. Any unbound material is then washed away or allowed to drain away. If the enzyme is present in the sample then the modification region 14 is cleaved and the binding member 16 is unable to bind the substrate 10 and thus the reporter 18 is not immobilised on the solid support. Therefore, the presence of the enzyme in the sample is indicated by the absence of the reporter from the solid support. If the enzyme is not present in the sample then the binding member 16 binds the substrate 10 and thus immobilises the reporter 18 on the solid support. Accordingly, the absence of the enzyme from the sample is indicated by the presence of the reporter 18 immobilised on the solid support.

In some embodiments, this type of procedure is carried out in 96-well microtitre plates in a manner well known to those skilled in the art. Alternatively, the procedure may be carried out in robotic systems using a variety of solid-phase capture materials, or with micro-array systems.

EXEMPLIFICATIONS

Example 1

A kit comprises the following components:—

1) A swab on a stem for the collection of a sample fluid (e.g. from a wound).

2) A lateral flow test-strip, which is mounted in a plastic case. The test strip has a first detection zone which comprises streptavidin adsorbed as a first test line across the flow-path of the test strip and a second detection zone which comprises anti-sheep antibodies adsorbed as a second test line across the flow-path of the test strip, downstream of the first test line. There is an observation window in the plastic case through which to view the first and second test lines. There is also an integrated sample receiving pad, upstream of the first test line. In addition, the test strip has gold particles bearing sheep antibodies (substrate recognition molecules) dried into the test strip between the sample-receiving pad and the first test line or dried into the sample-receiving pad itself.

3) A test tube, in which the swab may be placed, together with sample-extraction buffer and substrate. The test-tube is constructed with a flip-top spout, which is snapped in place when the sample/extraction-fluid/substrate mixture is ready to be dispensed onto the test strip. The sample may be applied drop-wise from the inverted tube, through the spout.

4) Extraction fluid consisting of phospahate buffered saline (PBS) at pH 7.2 and 0.1% Tween™ 20.

5) A substrate (which may be pre-dissolved in the extraction fluid). The substrate consists of a peptide containing a sequence of amino acids biased for MMP-9. The sequence (G)PQGIFG(Q) (SEQ ID NO: 1) is especially suitable, but many others are available and these can be derived from the scientific literature. The substrate carries a terminal biotin group, connected via a polyethylene glycol spacer/linker. The peptide is recognised by the sheep antibodies to which the gold particles are attached.

The procedure for use of the kit is as follows:—

STEP 1: A sample of fluid (the test sample) is collected by means of the swab supplied with the kit. The swab, bearing the fluid sample, is placed in the test-tube with the extraction buffer and a defined amount of substrate (the precise amount of substrate is important, as it must be a limiting quantity that only just saturates the first line when there is no enzyme present in the test sample). The swab is rotated vigorously within the extraction fluid in order to release the fluid sample so that it can mix with the ligand. This reaction mixture is incubated at ambient temperature for a defined period of time (e.g. 10 minutes).

STEP 2: At the end of the incubation period, the swab is either removed or the stem is snapped off, and the spouted lid is placed on the top. The tube is then inverted and squeezed so that four drops of liquid are dropped onto the sample receiving pad. As the liquid migrates into the test strip, it contacts the dried sheep antibodies attached to gold particles. These are re-hydrated by the test sample, whereupon the sheep antibodies bind to any un-modified substrate. As the liquid and gold particles move through the lateral-flow test strip they meet the first line, where biotin (on the substrate) is recognised and captured. Any gold particles bound to intact substrate are captured on this first line, via the terminal biotin of the substrate. Those that are not bound to the substrate, or are bound to a cleaved substrate pass through to be captured at the second (anti-sheep) line.

The user observes the lines that have formed and assesses their relative intensities. The absence of a first line and the presence of a full strength second line indicates a high level of protease in the test sample. The opposite result indicates a zero or low level of protease, below the detectable limit. Stages in between these extremes indicate different levels of protease in the test sample. In some embodiments, the result is read by means of an opto-electronic strip reader, and the readings are automatically interpreted by a simple algorithm with a simple result presented to the user.

In a variation of this example, the gold particles (bearing the sheep antibodies) are added to the reaction mixture at the end of the incubation period, instead of their being incorporated into the test strip.

(iv) mixing the sample and substrate such that at least some of the enzyme in the sample modifies the substrate; and
(v) bringing the substrate and the substrate recognition molecule into contact and detecting the presence of the label wherein detection of the label indicates the absence of the enzyme.

2. A method of delecting an enzyme capable of modifying a substrate comprising the steps of:
(i) providing a substrate comprising an attachment region and a modification region sensitive to modification by the enzyme from an unmodified state to a modified stale;
(ii) providing a sample suspected of containing the enzyme;
(iii) providing a substrate recognition molecule to which is coupled a detectable label, wherein the substrate recognition molecule specifically binds the modification region in the unmodified state, the binding site of the substrate recognition molecule being such that the modification region of the substrate is preferentially bound by said substrate recognition molecule as compared with the enzyme when the substrate, substrate recognition molecule and enzyme are mixed, and wherein the substrate recognition molecule sequesters the modifiable region of the substrate, and in doing so it prevents the enzyme from modifying the substrate further;

---

---

The invention claimed is:

1. A method of detecting an enzyme capable of modifying a substrate comprising the steps of:
   (i) providing a substrate comprising an attachment region and a modification region sensitive to modification by the enzyme from an unmodified state to a modified state, providing a solid support and attaching the attachment region of the substrate to the solid support by providing a first capture recognition molecule, capable of binding the attachment region, on the solid support;
   (ii) providing a sample suspected of containing the enzyme;
   (iii) providing a substrate recognition molecule to which is coupled a detectable label, wherein the substrate recognition molecule specifically binds the modification region in the unmodified state, the binding site of the substrate recognition molecule being such that the modification region of the substrate is preferentially bound by said substrate recognition molecule as compared with the enzyme when the substrate, substrate recognition molecule and enzyme are mixed, and wherein the substrate recognition molecule sequesters the modifiable region of the substrate, and in doing so it prevents the enzyme from modifying the substrate further;
   (iv) mixing the sample and substrate such that at least some of the enzyme in the sample modifies the substrate;
   (v) depositing the substrate and the substrate recognition molecule on or in a chromatographic medium, wherein the chromatographic medium comprises a first capture recognition molecule immobilised on or in the chromatographic medium, the first capture recognition molecule being capable of binding the attachment region, bringing the substrate and the substrate recognition molecule into contact and detecting the presence of the label wherein detection of the label indicates the absence of the enzyme.

3. The method according to claims 1 or 2 wherein the attachment region is an unmodifiable ligand.

4. The method according to claim 2 further comprising a second capture recognition molecule immobilised on or in the chromatographic medium, the second capture recognition molecule being capable of binding the substrate recognition molecule, optionally in combination with a fragment of the substrate, wherein the method further comprises the step of detecting the presence of the substrate recognition molecule at the second capture recognition molecule.

5. The method according to claims 1 or 2 wherein the enzyme is a hydrolase, preferably a peptidase, lipase, nuclease, homo- or hetero-oligosaccharidedase, homo or hetero-polysaccharidase, carbohydrase, phosphatase, sulphatase, neuraminidase, esterase, DNAase, RNAase, a kinase, a glycosyl transferase, an oxidase, a reductase or a transaminase.

6. The method according to claims 1 or 2 wherein the label is covalently bound to the substrate recognition molecule; and/or wherein the label is a fluorophore, a gold particle, a chromogen, a luminescent compound, a radioactive compound, a visible compound, a liposome or other vesicle containing signal producing substances, an electroactive species, or a combination of an enzyme and its substrate.

7. The method according to claims 1 or 2 wherein step (i) further comprises providing an additional substrate, the additional substrate also comprising a modification region, the modification region of the substrate being sensitive to modification by a first enzyme, the modification region of the additional substrate being sensitive to modification by a second enzyme and wherein step (iii) further comprises providing an additional substrate recognition molecule, the additional substrate recognition molecule specifically binding the modification region of the additional substrate, in the unmodified state, the modification region of the additional substrate being preferentially bound by said additional substrate recognition molecule as compared with the second enzyme and wherein step (v) comprises detecting the interaction between the substrate and additional substrate and the substrate recognition molecule and additional substrate recognition molecule respectively.

8. An enzyme detection device for carrying out the method according to claim 1 or claim 2.

9. The method according to claim 1 further comprising a second capture recognition molecule immobilised on or in the solid support, the second capture recognition molecule being capable of binding the substrate recognition molecule, optionally in combination with a fragment of the substrate, wherein the method further comprises the step of detecting the presence of the substrate recognition molecule at the second capture recognition molecule.

* * * * *

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Pro Gln Gly Ile Phe Gly Gln
1               5
```